United States Patent
Hayashi et al.

(10) Patent No.: US 7,189,330 B2
(45) Date of Patent: Mar. 13, 2007

(54) METHOD OF PRODUCING HYDROGEN RICH WATER AND HYDROGEN RICH WATER GENERATOR

(76) Inventors: Hidemitsu Hayashi, B-107, 2-4, Gakuenhigashimachi, Nishi-ku, Kobe-shi, Hyogo (JP); Chisato Daimaru, Takano Daiichi Blg.5F, 6-19-15, Jingumae, Shibuya-ku, Tokyo (JP)

(*) Notice: Subject to any disclaimer, the term of this patent is extended or adjusted under 35 U.S.C. 154(b) by 290 days.

(21) Appl. No.: 10/892,315

(22) Filed: Jul. 16, 2004

(65) Prior Publication Data

US 2005/0121399 A1 Jun. 9, 2005

(30) Foreign Application Priority Data

Dec. 3, 2003 (JP) ............................. 2003-404131

(51) Int. Cl.
*C02F 1/70* (2006.01)
(52) U.S. Cl. .................. 210/757; 210/764; 210/205; 210/501; 423/657
(58) Field of Classification Search ................ 210/205, 210/484, 501, 510.1, 757, 764; 252/176, 252/188.25; 428/550, 566; 422/277; 423/657
See application file for complete search history.

(56) References Cited

U.S. PATENT DOCUMENTS 2,623,812 A * 12/1952 Eborall et al. .............. 423/658
4,787,973 A * 11/1988 Ando et al. ................. 210/282
5,215,659 A * 6/1993 Ando ......................... 210/282

* cited by examiner

*Primary Examiner*—Matthew O. Savage
(74) *Attorney, Agent, or Firm*—Wenderoth, Lind & Ponack, LLP

(57) ABSTRACT

An object of this invention is to change room temperature or cooling drinking water to hydrogen rich water that contains hydrogen abundantly simply and efficiently without using an electrolytic device, and a hydrogen rich water generator 2 is provided by filling magnesium grain 4 that generates hydrogen gases by reacting with the drinking water 6 and silver grain 3 into the case 1 made of ceramics of water permeability and porosity. This hydrogen rich water generator 2 together with the drinking water 6 are filled in the vessel 5, and the drinking water 6, magnesium grain 4 and the ceramics and the silver grain 3 are caused to react in the vessel 5 to generate the hydrogen gases, and the drinking water 6 in the vessel 5 is purified by the reaction of the silver grain 3 and is changed to the hydrogen rich water having hydrogen abundantly and anti-bacterial action.

6 Claims, 2 Drawing Sheets

METHOD OF PRODUCING HYDROGEN RICH WATER AND HYDROGEN RICH WATER GENERATOR

BACKGROUND OF THE INVENTION

The present invention relates to a method of producing hydrogen rich water that is effective in an improvement of spots or wrinkles resulting from an elimination of active oxygen in the body by drinking or coating on skin or aging of the skin and to a hydrogen rich water generator.

A theory that water containing hydrogen in large quantity is effective in the elimination of the active oxygen that is considered to be of a cause of cancers and a variety of diseases has been made public recently in medical circles, and has drawn attentions among the circles.

As a device for producing drinking water of rich contents of hydrogen, devices utilizing electrolysis have been known in the general public.

Furthermore, heretofore, regarding magnesium, the following concepts are considered. [Metal magnesium is not immersed or dissolved in water at room temperature, but when fine powder is heated in the water, magnesium hydroxide and hydrogen gases are generated by reacting with water. . . . ] (For example, refer to page 82 of Kodansha Shuppan Co., Ltd. <<New knowledge of element 11 1>> author—Mr. Hiroshi Sakurai) or [Magnesium Mg . . . reacts with steam of high temperature to generate hydrogen . . . ] (For example, refer to page 64 of 2002 year Education Seminor, Education Television, NHK High School Chair, Chemistry, edited by Japan Broadcasting Association (NHK). NHK Publication Association, issued by NHK Publication Association) conventional hydrogen rich water generator utilizing the electrolysis needs electric power source, and moreover, its structure becomes complicated, and results in high cost and has being unable to supply hydrogen rich water simply and at low cost to the consumers.

An object of the present invention is to solve this issue.

Furthermore, another object of the present invention is to provide a hydrogen rich water generator with an improved hydrogen generating function by utilizing characteristics of ceramics.

SUMMARY OF THE INVENTION

The present invention is characterized by reacting the drinking water with water permeable magnesium grain stored in a vessel made of ceramic to generate hydrogen gases and by converting the drinking water to hydrogen rich water that contains rich hydrogen.

Furthermore, the present invention is characterized in that the ceramics has a porosity.

Moreover, the present invention is designed to react the drinking water with the magnesium and silver grain and the hydrogen rich water is purified by the silver grain.

In addition, the present invention is characterized in that the drinking water is either at room temperature or cooling water.

Yet furthermore, the present invention comprises a case made of ceramics of cylindrical shape to which water can permeate which can be fitted into a vessel for drinking water and magnesium grain stored in a hollow portion of the case and generates hydrogen gases by reacting with the drinking water.

Finally, the present invention stores the magnesium grain together with silver grain for purifying the drinking water in the case.

DETAILED DESCRIPTION OF THE INVENTION

Figure 1:
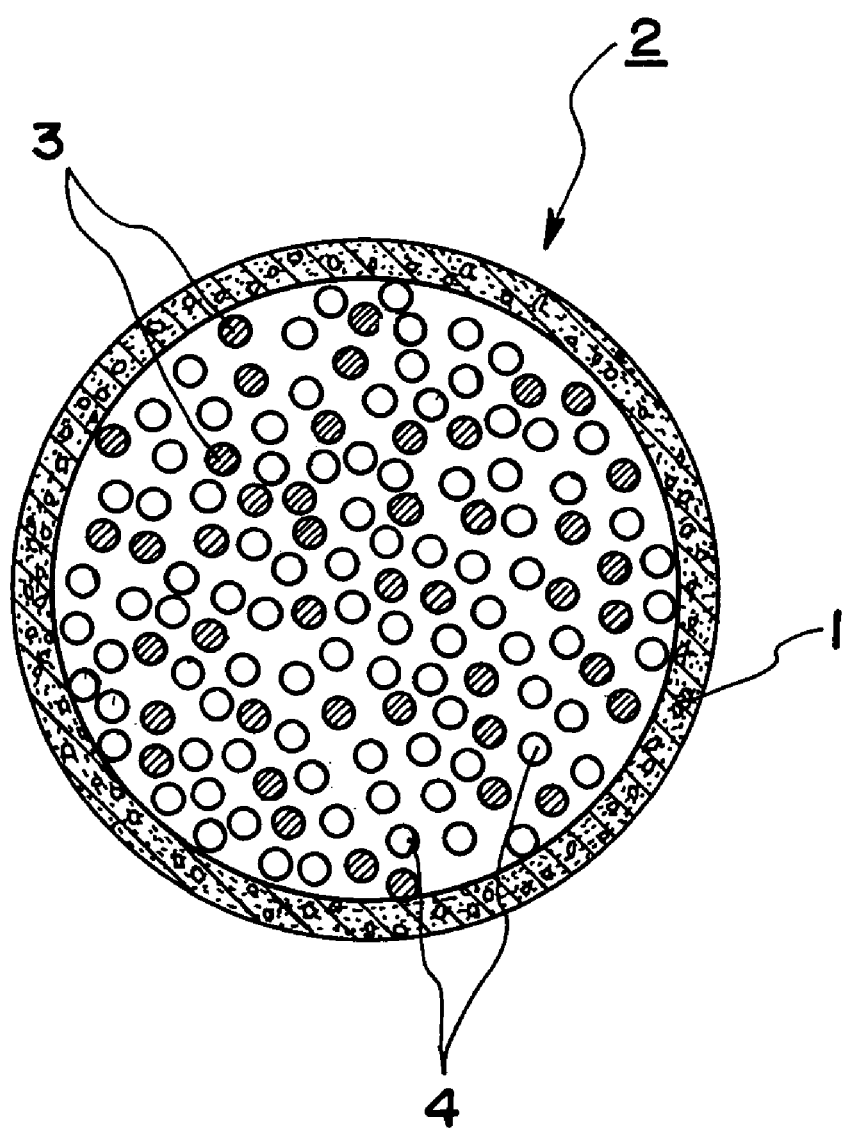
FIG. 1 is a cross sectional explanatory drawing of hydrogen rich water generator according to the present invention.

In the drawings, reference numeral 1 denotes bullet type case in a hydrogen rich water case in a hydrogen rich water generator 2, and the inside and the outside of the cases communicate through numerous small holes formed on the cases 1, and the liquid freely moves in and out of the case 1.

In the case 1, silver grain 3 whose size is bigger than the small holes of an outer shell of the case 1, and magnesium grain 4 are filled in predetermined quantities.

Figure 2:
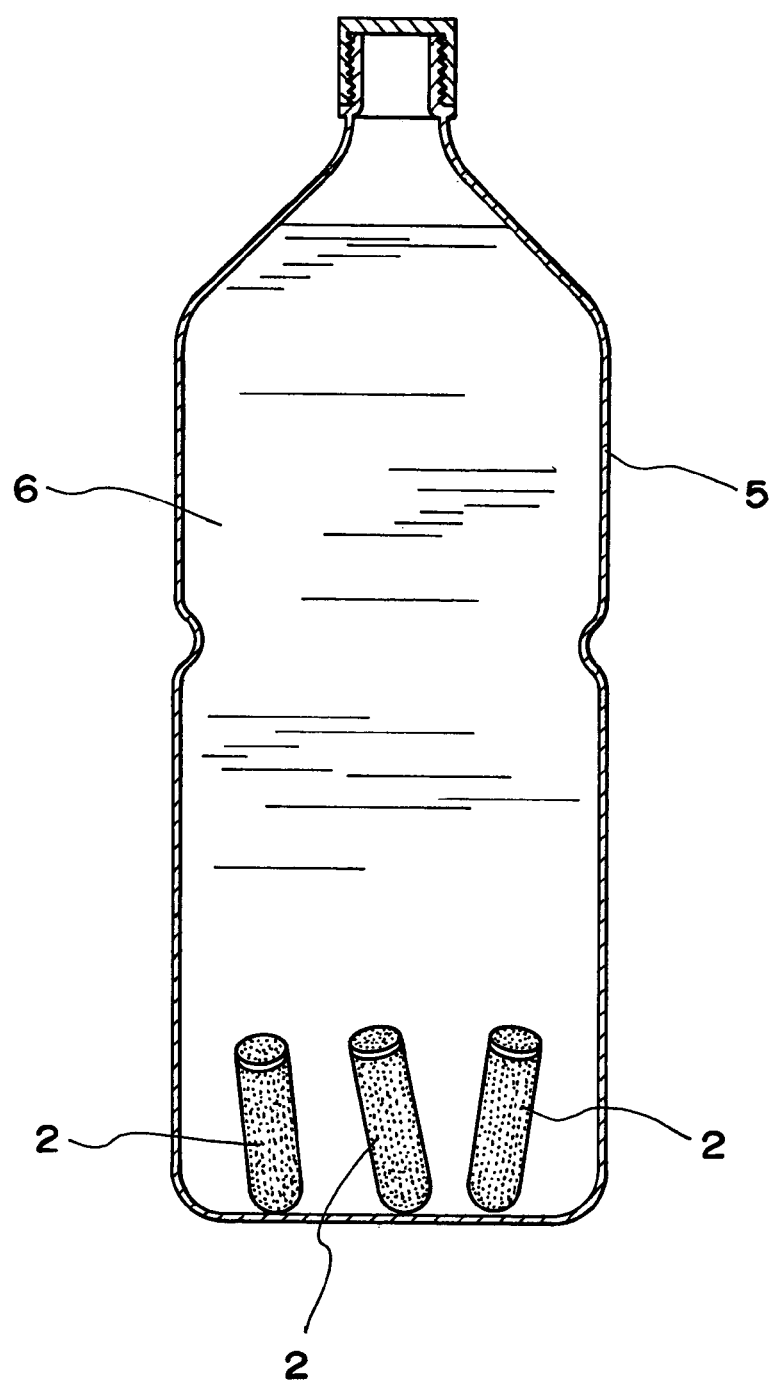
FIG. 2 is an explanatory drawing of the entire generator of the present invention.

In the foregoing construction, as shown in FIG. 2, the hydrogen rich water generator 2 that contains the case 1 filled with the silver grain 3 and the magnesium grain 4 is charged into a vessel 5 that contains drinking water 6 of room temperature or cooling temperature. After charging the hydrogen rich water generator 2, in about 10 minutes, the drinking water 6 in the vessel 5 reacts with the silver grain 3 so that the water is purified. Furthermore, the drinking water 6 reacts with the magnesium grain 4 simultaneously and generates hydrogen gases by the following chemical formula.

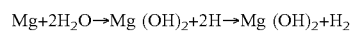

$$Mg+2H_2O \rightarrow Mg(OH)_2+2H \rightarrow Mg(OH)_2+H_2$$

As a result, the drinking water 6 such as room temperature or cooling water in the vessel 1 is purified and simultaneously, becomes the hydrogen rich water. At present, the metal magnesium generates the hydrogen gases by the reaction with the water when the metal is heated or the magnesium generates the hydrogen gases by the reaction with high temperature steam which is said to be the established theory in chemistry circles. However, when the reaction of the magnesium grain in the foregoing embodiment, is inspected, the magnesium easily reacts with the room temperature (about 25 centigrade) or cooling water (about 5 centigrade) to generate magnesium hydroxide and hydrogen gases and this reaction has been newly recognized.

From this discovery, the hydrogen rich water can be produced positively and at low cost without using an electrolytic device.

The molecule or particle of water is pulverized by a discharge of electron and far-infrared ray effect of the ceramics that is the structural material of the case along with hydrogen generating phenomenon caused by the reaction with the magnesium grain and the water, whereby the water is activated. The water activating performance against the water molecule is an extremely important fundamental performance of the ceramics. This performance test is conducted in such a way that the size of the molecule is judged by a frequency illustrated on a diagram of vector prepared by resonating how small the molecule of water or oil becomes with a nuclear magnetic resonating device.

Now, a matter of discussion comes to a comparison of untreated water or oil and water and oil treated with the ceramics, but it can be judged by how small it becomes when compared with the original frequency. The ceramics used in the embodiment of the present invention shows an excellent numerical value like 63.9 HZ. The emissivity curve of the far-infrared rays of the ceramics that activates the water is considered to be ideal if it draws a smooth curve. The ceramics used in the embodiment of the present invention materializes a radiation curve characteristics close to the ideal with a minimum distance from the standard line. The ceramics used in the embodiment of the present invention generates $H_2O_2$ hydrogen peroxide water when the water is activated.

This $H_2O_2$ hydrogen peroxide water is used as so called disinfectant solution but the water is produced in a quantity almost a double of normal tap water in the water treated by the ceramics of the embodiment of the present invention.

This quantity is so small quantity giving no harm to human being or animals, but becomes a threat to bacteria. When *coli bacillus*, bleeding *coli bacillus* 0–157, yellow *staphylococcus* are cultivated in the water treated by the ceramics of the embodiment of the present invention for 48 hours, whereby it can be reduced by 99.6% to 99.9%. As described in the foregoing, the water activated by the ceramics has sterilizing power. Also, the ceramics in the drinking water reacts with the magnesium, and promotes the generation of the hydrogen by the magnesium, and a large quantify of the hydrogen gas is confirmed to be generating in the drinking water.

For reference, in case PP, namely, polypropylene is used as the material of the case 1, there is a case where allergy is caused against the ingredient of the poly propylene dissolved from this case, but like the embodiment of the present invention, in case the ceramics is used the ceramics seldom causes allergy so that the problem of the allergy can be solved. Moreover, as described in the foregoing, the ceramics promotes the activation of water and the generation of hydrogen gases and also, produces anti-bacterial action in the hydrogen rich water.

The present invention can change the normal drinking water to the hydrogen rich water simply and efficiently by the method and the device of the present invention described in the foregoing.

What is claimed is:

1. A method of producing hydrogen rich water which comprises generating hydrogen gases by reacting room temperature or cooled drinking water with magnesium grains stored in a case made of ceramics inside a vessel, wherein the water is capable of permeating into the inside of the case, and changing the drinking water to hydrogen rich water that contains abundant hydrogen.

2. A method of producing hydrogen rich water according to claim 1 wherein the ceramics has porosity.

3. A method of producing hydrogen rich water according to claim 1 wherein the case further contains silver grains, and the drinking water is caused to react with the silver grains, and the hydrogen rich water is purified by the silver grains.

4. A hydrogen rich water generator which comprises a case made of ceramics in cylindrical shape and having a hollow portion and which is chargeable into a vessel for drinking water, wherein the case is capable of permeation by water into the hollow portion of the case, and magnesium grains stored in the hollow portion of the case which generate hydrogen gases by reaction with room temperature or cooled drinking water.

5. A hydrogen rich water generator according to claim 4 wherein the cermics has porosity.

6. A hydrogen rich water generator according to claim 4 wherein the case further contains silver grains for purifying the drinking water.

* * * * *